US009389173B2

(12) United States Patent
Tian (10) Patent No.: US 9,389,173 B2
(45) Date of Patent: Jul. 12, 2016

(54) METHOD FOR DETECTING RESISTANCE OF A PHOTO RESIST LAYER (71) Applicant: BOE TECHNOLOGY GROUP CO., LTD., Beijing (CN)

(72) Inventor: Hui Tian, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 14/434,187

(22) PCT Filed: Aug. 15, 2014

(86) PCT No.: PCT/CN2014/084507
§ 371 (c)(1),
(2) Date: Apr. 8, 2015

(87) PCT Pub. No.: WO2015/143821
PCT Pub. Date: Oct. 1, 2015

(65) Prior Publication Data
US 2016/0061722 A1 Mar. 3, 2016

(30) Foreign Application Priority Data
Mar. 24, 2014 (CN) .......................... 2014 1 0109564

(51) Int. Cl.
H01L 21/66 (2006.01)
H01L 21/027 (2006.01)
(Continued)

(52) U.S. Cl.
CPC .............. G01N 21/41 (2013.01); G01N 21/211 (2013.01); H01L 21/0273 (2013.01); H01L 21/31058 (2013.01); H01L 21/31155 (2013.01); H01L 22/12 (2013.01); G01N 2201/0683 (2013.01)

(58) Field of Classification Search
CPC ..................... H01L 21/0273; H01L 21/31058; H01L 21/31155
See application file for complete search history.

(56) References Cited

U.S. PATENT DOCUMENTS

| 6,141,103 A | 10/2000 | Pinaton et al. | |
|---|---|---|---|
| 2010/0302547 A1* | 12/2010 | Moll | G01N 21/55 356/445 |
| 2014/0099783 A1* | 4/2014 | Lai | H01L 21/266 438/514 |

FOREIGN PATENT DOCUMENTS

| CN | 102376541 A | 3/2012 |
|---|---|---|
| CN | 102403245 A | 4/2012 |

(Continued)

OTHER PUBLICATIONS

English Translation of the Written Opinion of the International Search Authority for PCTCN2014084507, 3 pages.

(Continued)

Primary Examiner — Mamadou Diallo
(74) Attorney, Agent, or Firm — Kinney & Lange, P.A.

(57) ABSTRACT

The present disclosure provides a method for detecting resistance of a photo resist layer. The method includes: providing a silicon wafer and measuring a refractive index of a surface of the silicon wafer as an initial refractive index of the surface of the silicon wafer; forming photo resist layers with different thicknesses on the surface of the silicon wafer; performing ion-implantation on the photo resist layers by predetermined amounts; peeling off the photo resist layers from the surface of the silicon wafer; and testing the refractive indexes of different areas on the surface of the silicon wafer after the ion-implantation, on which the photo resist layers with different thicknesses are located and determining the resistance of the photo resist layers with different thicknesses in contrast to the initial refractive index before the ion-implantation.

19 Claims, 4 Drawing Sheets (51) Int. Cl.
  *G01N 21/41* (2006.01)
  *G01N 21/21* (2006.01)
  *H01L 21/3105* (2006.01)
  *H01L 21/3115* (2006.01)

(56) References Cited

FOREIGN PATENT DOCUMENTS

| CN | 102449431 A | 5/2012 |
|---|---|---|
| CN | 102706785 A | 10/2012 |
| CN | 102903649 A | 1/2013 |
| CN | 103441086 A | 12/2013 |
| CN | 103887200 A | 6/2014 |
| JP | 10-083970 A | 3/1998 |

OTHER PUBLICATIONS

International Search Report in Chinese dated Nov. 27, 2014 for corresponding PCT Application No. PCT/CN2014/084507.
Written Opinion in Chinese dated Dec. 23, 2014 for corresponding PCT Application No. PCT/CN2014/084507.
First Chinese Office Action, Chinese Application No. 201410109564.9, dated Feb. 3, 2016.
Second Chinese Office Action dated Apr. 14, 2016, for corresponding Chinese Application No. 201410109564.9.

* cited by examiner

METHOD FOR DETECTING RESISTANCE OF A PHOTO RESIST LAYER

BACKGROUND OF THE INVENTION

1. Field of the Invention

The present disclosure relates to the technical field of liquid display, in particular to a method for detecting resistance of a photo resist layer.

2. Description of the Related Art

The ion-implantation process is a doping technology for semiconductor material. It means that an ion beam has a speed that is reduced gradually due to resistance of solid material after the ion beam impacts on the solid material and the ion finally is left in the solid material. The ion-implantation process has advantages of low temperature doping, easy masking, accurate dose control and high uniformity. In addition, it may be used in a plurality of process steps, for example, source and drain doping, channel doping, light doping or drain doping. In this way, the resultant semiconductor devices will have properties such as high speed, low power assumption, good stability and high yield. In different ion-implantation processes, the conditions such as the desired energy and doses of the ion beam are different. And the doping is performed in specific areas when the ions are implanted while other positions or the remaining areas are shielded by resist layers such as photo resist. The photo resist layers are most popular. The photo resist layers with different thicknesses have different resistances to the ion-implantation. Low thickness of the photo resist layer may cause the ions to penetrate through the photo resist layer easily while high thickness of the photo resist layer may bring the difficulty of controlling the critical dimension in lithography. Thus, it is desired to select a suitable thickness of the photo resist layer in the ion-implantation.

Figure 1:
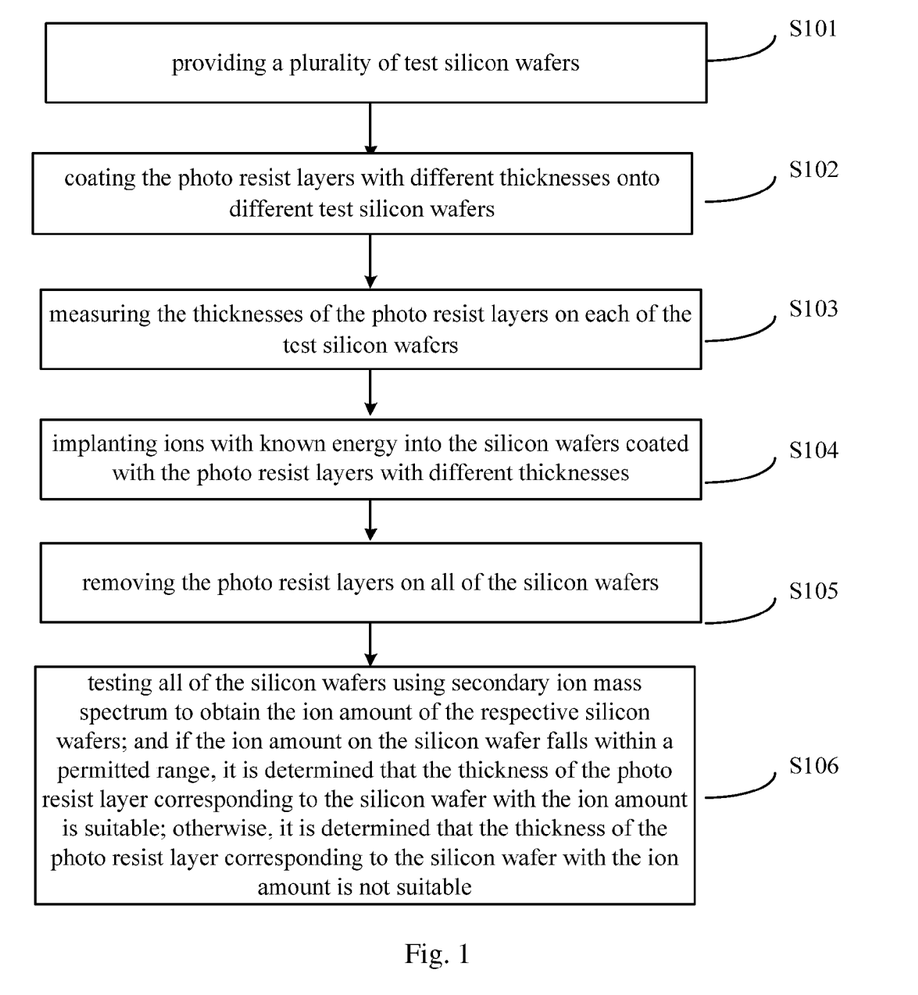
FIG. 1 is a flow chart showing steps of a method for determining resistance of a photo resist layer in the prior art.

In the prior art, a method for determining the resistance of a photo resist layer includes the following steps as shown in FIG. 1. In particular, it includes: Step S101 of providing a plurality of test silicon wafers, which are desired because resistance of the photo resist layer in a plurality of areas needs to be determined and each area needs one test silicon wafer; Step S102 of coating the photo resist layers with different thicknesses onto different test silicon wafers; Step S103 of measuring the thickness of the photo resist layers on each of the test silicon wafers; Step S104 of implanting ions with known energy into the silicon wafers coated with the photo resist layers with different thicknesses; Step S105 of removing the photo resist layers on all of the silicon wafers; Step S106 of testing all of the silicon wafers using secondary ion mass spectrum or spectrometer to obtain the ion amount of the respective silicon wafers. If the ion amount on the silicon wafer falls within a permitted range, it will be determined that the thickness of the photo resist layer coated on the silicon wafer is suitable; otherwise, it will be determined that the thickness of the photo resist layer coated on the silicon wafer is not suitable.

As discussed above, in order to determine the resistance or resisting capability of the photo resist layer to the ion-implantation, at least a plurality of test silicon wafers are needed to perform the above operations and then the ion amount on the test silicon wafers need to be measured one by one. Such method has the following defects: on one hand, a great deal of test silicon wafers are needed, which causes undue cost of detecting the photo resist layers, due to the high manufacturing cost of the test silicon wafers; on the other hand, the secondary ion mass spectrometry is a very expensive test means and the production of test samples is complicated and it will take much test time, thereby, the evaluation cost and time may be greatly increased.

SUMMARY OF THE INVENTION

An object of the present invention is to provide a method for detecting resistance of a photo resist layer, which can at least partially achieve reduction in difficulty of finding an optimum thickness of the photo resist layer and reduce the detection costs.

In accordance with an aspect of the present disclosure, it provides a method for detecting resistance or resistance to ion of a photo resist layer comprising steps of:

providing a silicon wafer and measuring a refractive index of a surface of the silicon wafer as an initial refractive index of the surface of the silicon wafer;

forming photo resist layers with different thicknesses on the surface of the silicon wafer;

performing ion-implantation on the photo resist layers by predetermined amounts;

peeling off the photo resist layers from the surface of the silicon wafer; and testing the refractive indexes of different areas on the surface of the silicon wafer after the ion-implantation, on which the photo resist layers with different thicknesses are located and determining the resistance of the photo resist layers with different thicknesses in contrast to the initial refractive index before the ion-implantation.

In an embodiment, the step of forming photo resist layers with different thicknesses on the surface of the silicon wafer comprises:

coating photo resist onto the surface of the silicon wafer to form the photo resist layers.

In an embodiment, the step of forming photo resist layers with different thicknesses on the surface of the silicon wafer further comprises:

exposing the photo resist layers coated on the different areas on the surface of the silicon wafer for different exposure periods and developing them to form the photo resist layers with different thicknesses.

In an embodiment, the step of forming photo resist layers with different thicknesses on the surface of the silicon wafer further comprises:

measuring the thicknesses of the photo resist layers on the different areas.

In an embodiment, a pre-baking process for the silicon wafer is performed after coating the surface of the silicon wafer with photo resist.

In an embodiment, the pre-baking process is performed at a temperature of 10-150° C. and for 10-300 seconds.

Preferably, the pre-baking process is performed by low temperature heating provided by an infra-red oven.

In an embodiment, the thicknesses of the photo resist layers change continuously in steps from a center of the surface of the silicon wafer to its edge.

In an embodiment, the predetermined amounts comprise predetermined energy and doses.

In an embodiment, the refractive indexes of the surface of the silicon wafer before and after the ion-implantation are measured by ellipsometry.

In an embodiment, the tests for the refractive indexes before the ion-implantation and after the ion-implantation have the same testing condition and environment.

In an embodiment, after the step of testing the refractive indexes of different areas on the surface of the silicon wafer after the ion-implantation, the method further comprises:

calculating differences between the refractive indexes of the corresponding areas on the surface of the silicon wafer covered by the photo resist layers with different thicknesses after the ion-implantation and the initial refractive index before the ion-implantation, and if one of the differences has an absolute value range of 0-0.02, it is determined that the photo resist layer with a corresponding thickness is resistant sufficiently and efficiently (to ion) and that such a corresponding thickness is an effective thickness of the photo resist layer.

In an embodiment, the thickness corresponding to the minimum absolute value of the differences of the refractive indexes of the surface of the silicon wafer after the ion-implantation and before the ion-implantation is selected from all of the effective thicknesses of the photo resist layers as the optimum thickness of photo resist layers.

In an embodiment, if the absolute value of the difference of the refractive indexes is greater than 0.02, it is determined that the photo resist layer with the corresponding thickness fails to be efficiently resistant.

DETAILED DESCRIPTION OF PREFERRED EMBODIMENTS OF THE INVENTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The embodiments of the present invention will be further explained below with reference to the figures and examples. The following embodiments are only explained by way of examples, instead of being intended to limit the scope of the present invention.

The principle of ion-implantation is that atoms or molecules are ionized to form ions, i.e., plasma, which can have certain charges. The ions may be accelerated by an electrical field and the direction of movement of the ions may be changed using a magnetic field to form an ion beam. In this way, it may control ions to enter inside of the silicon wafer while remaining a certain energy to achieve the object of doping. After the ions are implanted into the silicon wafer, the ions may be impacted on silicon atoms to lose energy. Once their energy is depleted, the ions will stop at certain positions in the silicon wafer. The ions transmit energy to the silicon atoms by impacting with the silicon atoms. And then the silicon atoms become new incoming particles which may also be impacted on other silicon atoms to form a chain reaction.

In an embodiment of the present invention, it provides a method for detecting resistance or resisting ability of a photo resist layer. The method may at least partially achieve detection of resistance of the photo resist layer of a surface of a silicon wafer easily, and finally attain the optimum thickness of the photo resist layer, so as to achieve good resistance after the ion-implantation.

Figure 2:
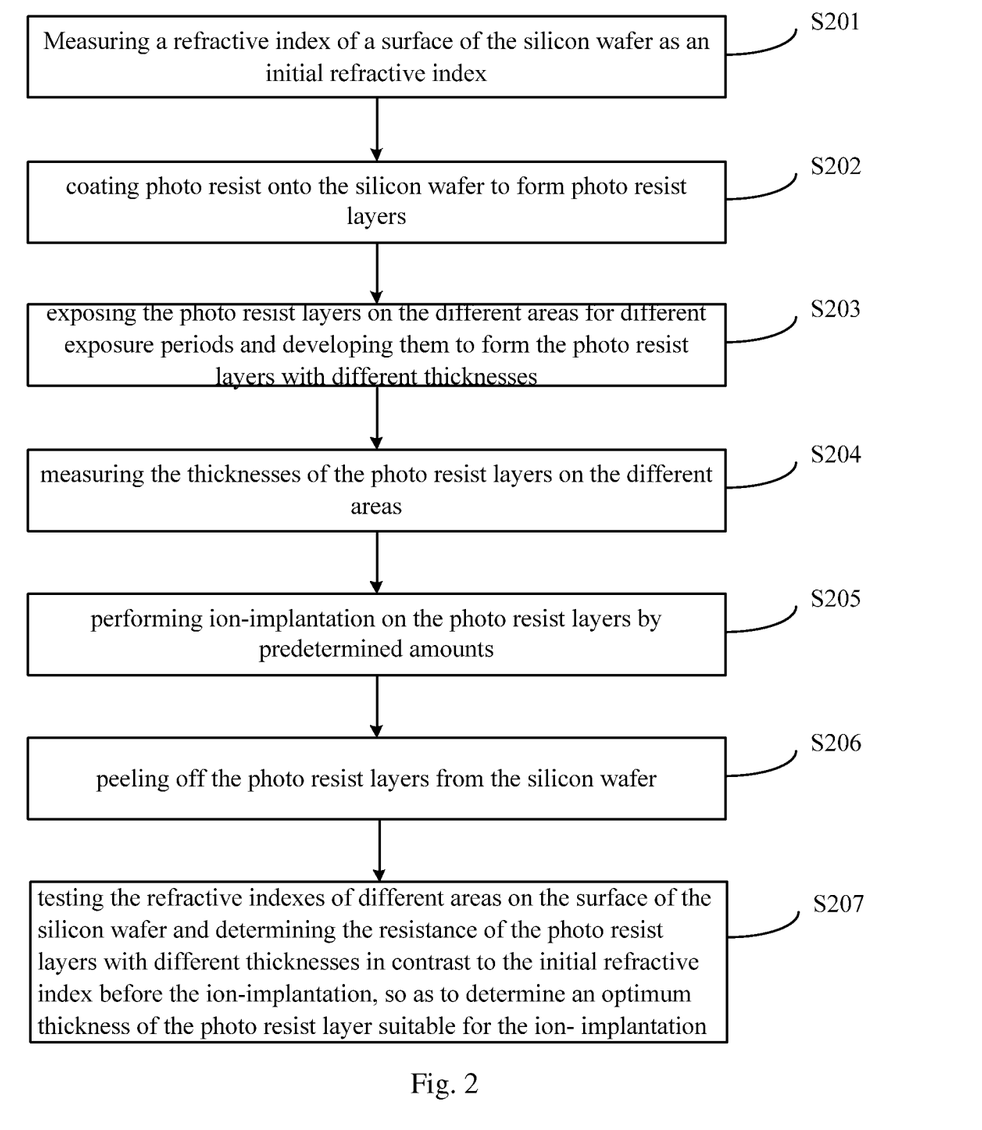
FIG. 2 is a flow chart showing steps of a method for detecting resistance of a photo resist layer according to an embodiment of the present invention.

FIG. 2 shows a flow chart of an example of the above method. Apparently, all of embodiments that can achieve the object of the present invention by using the basic inventive concept of the present invention fall within the scope of the present invention, instead of being only limited to the specific steps shown in FIG. 2. On other words, steps shown in FIG. 2 are only illustrative, and all of the embodiments of the present invention do not have to include these steps. Instead, it may only include part of those steps or cornel steps in those steps.

As an example, in another embodiment of the present invention, a method for detecting resistance of a photo resist layer includes: providing a silicon wafer and measuring refractive index of a surface of the silicon wafer as an initial refractive index of the surface of the silicon wafer; forming photo resist layers with different thicknesses on the surface of the silicon wafer; performing ion-implantation on the photo resist layers by predetermined amounts; peeling off the photo resist layers from the surface of the silicon wafer; and testing the refractive indexes of different areas on the surface of the silicon wafer on which the photo resist layers with different thicknesses are located after the ion-implantation and determining the resistance of the photo resist layers with different thicknesses in contrast to the initial refractive index before the ion-implantation.

Figure 3A:
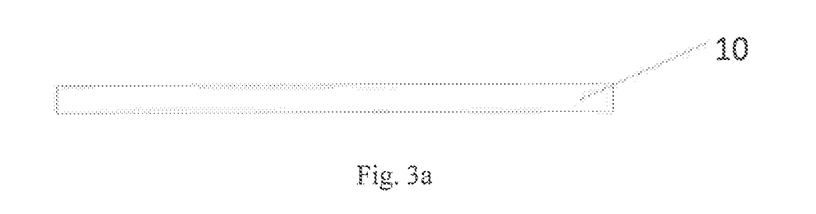
FIGS. 3a-3e are schematic views for showing a structure obtained at corresponding steps of FIG. 2.
Figure 3B:
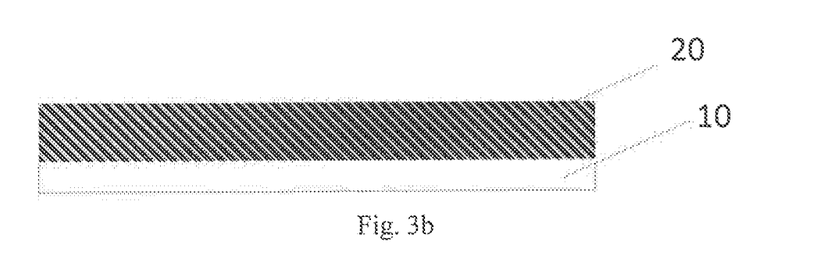
Figure 3C:
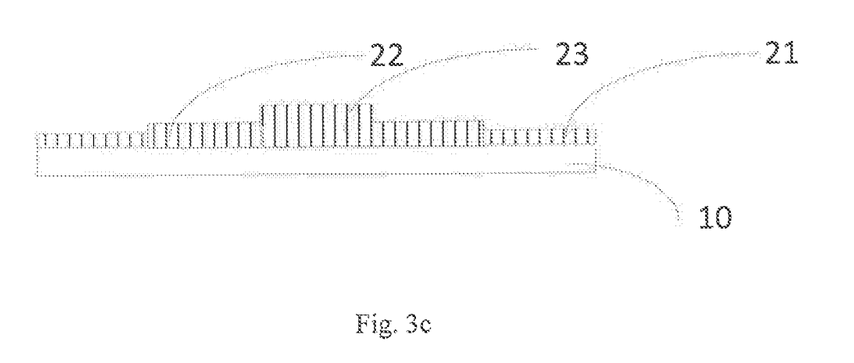
Figure 3D:
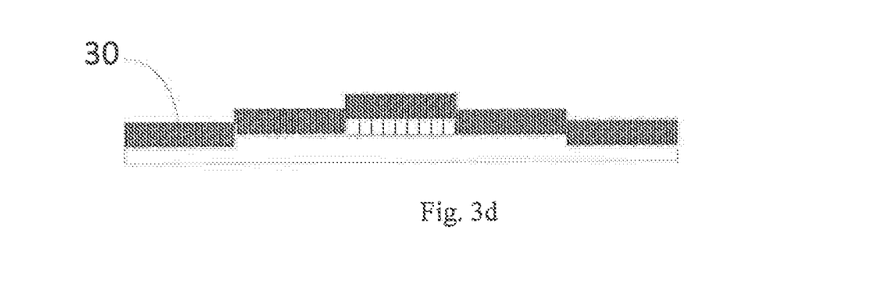
Figure 3E:
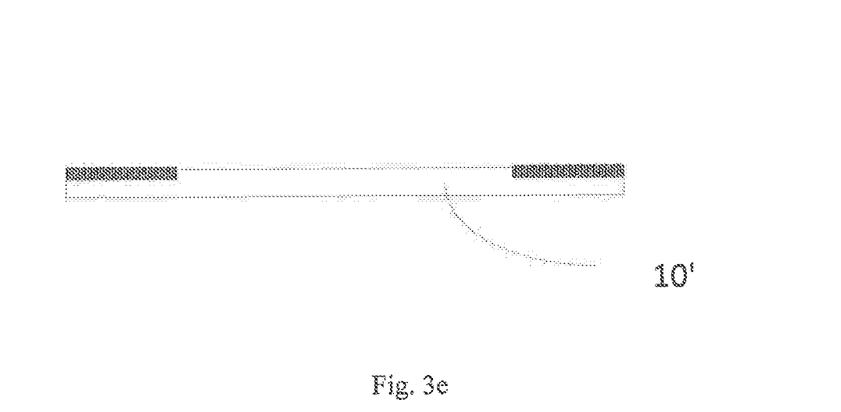

Specifically, the method shown in FIG. 2 includes the following steps: Step S201 of providing a silicon wafer 10 and measuring refractive index of a surface of the silicon wafer 10 as an initial refractive index of the surface of the silicon wafer 10, as shown in FIG. 3a;

Step S202 of coating photo resist onto the surface of the silicon wafer 10 to form photo resist layers 20, as shown in FIG. 3b;

Step S203 of exposing the photo resist layers 20 coated on the different areas on the surface of the silicon wafer 10 for different exposure periods and developing them to form the photo resist layers 21, 22, 23 with different thicknesses, as shown in FIG. 3c;

Step S204 of measuring the thicknesses of the photo resist layers 21, 22, 23 on the different areas;

Step S205 of performing ion-implantation 30 on the photo resist layers 21, 22, 23 by predetermined amounts, as shown in FIG. 3d;

Step S206 of peeling off the photo resist layers 21, 22, 23 from the surface of the silicon wafer 10; and Step S207 of testing the refractive indexes of different areas on the surface of the silicon wafer 10' as shown in FIG. 3e after peeling off the photo resist layers 21, 22, 23 and comparing the refractive indexes with the initial refractive index to determine the resistance of the photo resist layers 21, 22, 23 with different thicknesses. On basis of this, it may determine an optimum thickness of the photo resist layer suitable for the ion-implantation by the predetermined amounts.

Apparently, in contrast to the method discussed in the prior art that needs a plurality of test silicon wafers, the method described in the present disclosure only needs one silicon wafer, as the photo resist layers with different thicknesses may be obtained by exposing different areas on the surface of the silicon wafer for different exposure periods. And then, by comparing change of refractive indexes in the different areas of the surface of the silicon wafer after and before the ion-implantation, it may determine the resistance of the photo resist layers with different thicknesses coated on the different areas, and further find the optimum thickness of the photo resist layers, so as to save the evaluation time and cost efficiently.

In particular, in the Step S201, at first, a clean silicon wafer 10 is provided and the refractive index of the surface of the silicon wafer 10 is measured before the ion-implantation to obtain the initial refractive index of the surface of the silicon wafer, as shown in FIG. 3a.

In the Step S202, a layer of photo resist 20 is coated on the surface of the silicon wafer, and then a pre-baking process for the photo resist layer 20 on the silicon wafer is performed, as shown in FIG. 3b. Specifically, the pre-baking process is performed at a temperature of 10-150° C. and for 10-300 seconds.

The object of the pre-baking process is to facilitate volatilization of solvent in a film of the photo resist coated on the surface of the silicon wafer to increase adhesivity of the film of the photo resist to the surface of the silicon wafer. Typically, the pre-baking process is performed by low temperature heating provided by an infra-red oven such that it can be in a dry and unhardening state. In this way, chemical reactions may occur in the photo resist in the film of the photo resist in exposure. By the pre-baking process, the solvent in the photo resist layer may be evaporated to increase the adhesivity and control the sensitivity of the photo resist layer and the subsequent line width while releasing the residual internal stress in the photo resist layer.

In the Step S203, the exposure and development are performed, but the photo resist layers 20 coated on the different areas of the surface of the silicon wafer 10 are exposed for different exposure periods and developed to obtain the photo resist layers 21, 22, 23 with different thicknesses, as shown in FIG. 3c. Typically, the photo resist is coated on the surface of the silicon wafer in a liquid form, and becomes solid after exposure such that photo resist can protect the silicon wafer under it in the subsequent ion-implantation process. In addition, selecting different exposure periods for the exposure may achieve the photo resist layers with different thicknesses on the different areas on the surface of the silicon wafer. In particular, the longer the exposure period for the photo resist layer is, the lower the thickness of the resultant photo resist layer after development. It is because different exposure periods cause variation of solubility of the photo resist in a developer such that the resultant photo resist layers have different thicknesses.

In a further embodiment, the thicknesses of the photo resist layers change continuously in steps from a center of the surface of the silicon wafer to its edge as shown in FIG. 3c.

In the subsequent step S204, the thicknesses of the photo resist layers 21, 22, 23 on the different areas on the surface of the silicon wafer 10 are measured and recorded, for example, they may be recorded in sequence such that the resistance corresponding to each of the thicknesses of the photo resist layers may be calculated subsequently.

Then, in the step S205, the ion-implantation 30 is performed on the photo resist layer by the predetermined amounts, as shown in FIG. 3d. In this example, the predetermined amounts include predetermined energy and doses. Specifically, the magnitudes of the energy and doses may be selected on the basis of the specification of the ion-implantation apparatus. Typically, the energy of the ions selected for the ion-implantation apparatus having the conventional specification is in a range of 0-100 kv, and the doses of those are in a range of $0 \sim 1e^{16}$ cm$^{-3}$.

After the ion-implantation is finished, the Step S206 is performed to peel off the photo resist layers 21, 22, 23 from the silicon wafer 10. At last, the Step S207 is performed to test the refractive indexes of the different areas on the surface of the silicon wafer 10' as shown in FIG. 3e corresponding to the photo resist layer with different thicknesses. In contrast to the initial refractive index measured before the ion-implantation, the resistance of the photo resist layers with different thicknesses is determined. In view of this, it may also determine the optimum photo resist layer thickness suitable for the ion-implantation. In particular, it may include:

calculating a difference between the refractive indexes of the corresponding areas on the surface of the silicon wafer covered by the photo resist layers with different thicknesses after the ion-implantation and the initial refractive index of the same one area measured before the ion-implantation, and if the difference between the refractive indexes has an absolute value range of 0~0.02 (i.e., the range of −0.02~+0.02), it will be determined that the photo resist layers with the corresponding thicknesses are resistant sufficiently and efficiently and that the corresponding thicknesses are effective thicknesses of the photo resist layers. In addition, the thickness having the minimum absolute value of the difference of the refractive indexes of the surface of the silicon wafer after the ion-implantation and before the ion-implantation may be selected from all of the effective thicknesses of the photo resist layers as the optimum thickness of photo resist layers. As an example, in an embodiment, from all of suitable thicknesses of the photo resist layers, the thickness of the photo resist layer with the difference of refractive indexes which is closest to zero may be selected as the optimum thickness of the photo resist layer. If the absolute value of the difference of the refractive indexes is greater than 0.02, it will be determined that the photo resist layer with the corresponding thickness is not efficiently resistant. Please be noted that the range of difference of refractive indexes has a width of 0.02 herein, which is an empirical value. Further, in tests, errors between two tests, which may be caused by effects of factors such as systematic errors or the testing instrument, will be tiny, and thus, it will not affect the difference of the refractive indexes significantly.

In an example, the initial refractive index before the ion-implantation is defined as n1 and the refractive indexes in the different areas on the surface of the silicon wafer corresponding to the different thicknesses of the photo resist layers after the ion-implantation are defined as follows, the refractive index n2 being for the area in which the photo resist layer with thickness d1 is located, the refractive index n3 being for the area in which the photo resist layer with thickness d2 is located, . . . , and so on. Then, the difference between the refractive index in the area in which the photo resist layer with thickness d1 is located after the ion-implantation and the initial refractive index before the ion-implantation is calculated as $a1=n1-n2$. If $-0.02 \leq a1 \leq +0.02$, the photo resist layer with the thickness d1 will be resistant efficiently and thus the thickness d1 belongs to a suitable thickness of the photo resist layer. If $a1 > +0.02$ or $a1 < -0.02$, the photo resist layer with the thickness d1 will fail to be resistant efficiently. As such, the respective difference between refractive indexes in the areas on the surface of the silicon wafer in which the photo resist layers with the thicknesses d2 and d3 are located may be calculated similarly. As long as the difference between refractive indexes meets the range of −0.02~+0.02, the photo resist layer with such thickness will be suitable or efficient photo resist layer. Finally, the thickness of the photo resist layer with the difference of refractive indexes which is closest to zero may be selected from all the photo resist layers having suitable thicknesses, as the optimum thickness of the photo resist layer.

The detection method provided by the present embodiment has more accurate test results. On one hand, as the refractive index is an inherent parameter of material, the change of the refractive index caused by different implantation effects is very sensitive and the numerical value is relatively correct and stable; on the other hand, the errors introduced by the material of the silicon wafer itself may be eliminated by testing the difference of the two refractive indexes before the ion-implantation and after the ion-implantation.

It should be noted that the method, in the embodiment, the testing method of the refractive indexes of the surface of the silicon wafer after the ion-implantation and before the ion-implantation is ellipsometry, in which an elliptically polarized beam is projected onto the surface of the silicon wafer and the change of the polarization of the reflected beam is observed so as to determine the thickness and the refractive index of the film on the silicon wafer. In the conventional method for testing the thickness of the thin film, the ellipsometry is one of those that can measure the thinnest film and have the highest measurement precision. It is applied widely, such as in semiconductor industry, metal industry and biological field.

It should also be noted that the tests for the refractive indexes before the ion-implantation and after the ion-implantation have the substantially same testing condition and environment. Unless the tests for the refractive indexes before the ion-implantation and after the ion-implantation are performed at the substantially same testing condition and environment, it will not be ensured that the change of the refractive indexes (resistance to the ion-implantation) is only caused by the change of thickness of the photo resist layer.

As discussed above, in the method for detecting resistance of a photo resist layer, provided by the present embodiments, on one hand, the resistance of the photo resist layers with different thicknesses to the ion-implantation may be estimated by only one silicon wafer, so as to avoid coating the photo resist layer with different thicknesses at multiple times onto a plurality of test silicon wafers and save the costs of materials. On the other hand, as the ion-implantation into the silicon wafer may destroy the initial crystal structure of the silicon wafer such that the refractive indexes on the surface of the silicon wafer become large, it may be determined, from the change of refractive indexes on the surface of the silicon wafer after the ion-implantation and before the ion-implantation, whether the photo resist layer can be resistant efficiently or not, and the optimum thickness of the photo resist layer can be found. By this method, it may avoid use of the secondary ion mass spectrum or spectrometer which involves an expensive test costs and takes much time, in the prior art. Therefore, the method of the present disclosure may reduce the test cost and time significantly and reduce the detection periods.

The above exemplary embodiments are only used to explain the present disclosure, instead of limiting the present invention. It would be appreciated by those skilled in the art that various changes or modifications may be made in these embodiments without departing from the scopes and spirit of the present disclosure. Thus, all of equivalents should also fall within the scope of the present invention. The scope of the invention is defined in the appended claims.

What is claimed is:

1. A method for detecting resistance of photo resist layers, comprising steps of:
    providing a silicon wafer and measuring a refractive index of a surface of the silicon wafer as an initial refractive index of the surface of the silicon wafer;
    forming the photo resist layers with different thicknesses on the surface of the silicon wafer;
    performing ion-implantation on the photo resist layers by predetermined amounts;
    peeling off the photo resist layers from the surface of the silicon wafer; and
    testing refractive indexes of different areas on the surface of the silicon wafer after the ion-implantation, on which the photo resist layers with different thicknesses are located, and determining the resistance of the photo resist layers with different thicknesses in contrast to the initial refractive index before the ion-implantation,
    wherein after the step of testing the refractive indexes of different areas on the surface of the silicon wafer after the ion-implantation, the method further comprises:
    calculating differences between the refractive indexes of corresponding areas on the surface of the silicon wafer covered by the photo resist layers with different thicknesses after the ion-implantation and the initial refractive index before the ion-implantation, and if one of the differences has an absolute value range of 0-0.02, determining that the photo resist layer with a corresponding thickness is resistant sufficiently and efficiently and that such a corresponding thickness is an effective thickness of the photo resist layer.

2. The method according to claim 1, wherein the step of forming the photo resist layers with different thicknesses on the surface of the silicon wafer comprises:
    coating photo resist onto the surface of the silicon wafer to form the photo resist layers.

3. The method according to claim 2, wherein the step of forming the photo resist layers with different thicknesses on the surface of the silicon wafer further comprises:
    exposing the photo resist layers coated on the different areas on the surface of the silicon wafer for different exposure periods and developing them to form the photo resist layers with different thicknesses.

4. The method according to claim 3, wherein the step of forming the photo resist layers with different thicknesses on the surface of the silicon wafer further comprises:
    measuring the thicknesses of the photo resist layers on the different areas.

5. The method according to claim 2, wherein a pre-baking process for the silicon wafer is performed after coating the surface of the silicon wafer with photo resist.

6. The method according to claim 5, wherein the pre-baking process is performed at a temperature of 10-150° C. and for 10-300 seconds.

7. The method according to claim 6, wherein the pre-baking process is performed by low temperature heating provided by an infra-red oven.

8. The method according to claim 1, wherein the thicknesses of the photo resist layers change continuously in steps from a center of the surface of the silicon wafer to is an edge of the surface of the silicon wafer.

9. The method according to claim 1, wherein the predetermined amounts comprise predetermined energy and doses.

10. The method according to claim 1, wherein the refractive indexes of the surface of the silicon wafer before and after the ion-implantation are measured by ellipsometry.

11. The method according to claim 10, wherein the tests for the refractive indexes before the ion-implantation and after the ion-implantation have the same testing condition and environment.

12. The method according to claim 1, wherein the thickness corresponding to a minimum absolute value of the differences of the refractive indexes of the surface of the silicon wafer after the ion-implantation and before the ion-implantation is selected from all of the effective thicknesses of the photo resist layers as an optimum thickness of the photo resist layers.

13. The method according to claim 1, wherein if the absolute value of the difference of the refractive indexes is greater than 0.02, it is determined that the photo resist layer with the corresponding thickness fails to be efficiently resistant.

14. The method according to claim 4, wherein the thickness of the photo resist layers change continuously in steps from a center of the surface of the silicon wafer to an edge of the surface of the silicon wafer.

15. The method according to claim 7, wherein the thickness of the photo resist layers change continuously in steps from a center of the surface of the silicon wafer to an edge of the surface of the silicon wafer.

16. The method according to claim 4, wherein the refractive indexes of the surface of the silicon wafer before and after the ion-implantation are measured by ellipsometry.

17. The method according to claim 7, wherein the refractive indexes of the surface of the silicon wafer before and after the ion-implantation are measured by ellipsometry.

18. The method according to claim 8, wherein the refractive indexes of the surface of the silicon wafer before and after the ion-implantation are measured by ellipsometry.

19. The method according to claim 9, wherein the refractive indexes of the surface of the silicon wafer before and after the ion-implantation are measured by ellipsometry.

* * * * *